United States Patent
Lee et al.

(10) Patent No.: US 7,354,955 B2
(45) Date of Patent: Apr. 8, 2008

(54) (2S)-AMINO(PHENYL)ACETIC ACID AND DERIVATIVES AS $\alpha_2\delta$ VOLTAGE-GATED CALCIUM CHANNEL LIGANDS

(75) Inventors: Chih-Hung Lee, Vernon Hills, IL (US); Michael F. Jarvis, Vernon Hills, IL (US)

(73) Assignee: Abbott Laboratories, Abbot Park, IL (US)

( * ) Notice: Subject to any disclaimer, the term of this patent is extended or adjusted under 35 U.S.C. 154(b) by 448 days.

(21) Appl. No.: 10/752,943

(22) Filed: Jan. 7, 2004

(65) Prior Publication Data

US 2005/0148615 A1 Jul. 7, 2005

(51) Int. Cl.
A61K 31/195 (2006.01)
A61K 31/44 (2006.01)

(52) U.S. Cl. ..................................... 514/567; 514/282

(58) Field of Classification Search ............... 514/282, 514/567
See application file for complete search history.

(56) References Cited

U.S. PATENT DOCUMENTS 4,657,899 A * 4/1987 Rzeszotarski et al. ...... 514/120

FOREIGN PATENT DOCUMENTS

WO 02/30871 4/2002

OTHER PUBLICATIONS

Beers, M. H. and Berkow, R., Editors-in-Chief, The Merck Manual of Diagnosis and Therapy, 17th Edition, pp. 1363-1374, 1999.*
Klosa, J., "Morphinelike action of some spasmolytics on the central nervous system", abstract of Arch. Pharm. 286, pp. 218-219, 1953.*
Berge et al., "Pharmaceutical Salts," J. Pharmaceutical Sciences 66:1 et seq. (1977).
Brown et al., "Isolation of the [$^3$H]gabapentin-binding protein/$\alpha_2\delta$ $Ca^{2+}$ channel subunit from porcine brain: development of a radioligand binding assay for $\alpha_2\delta$ subunits using [$^3$H]leucine," Analytical Biochemistry 255:236-243 (1998).
Bryans et al., "3-Substituted GABA analogs with central nervous system activity: a review," Med. Res. Rev. 19:149-177 (1999).
Chaplan et al., "Quantitative assessment of tactile allodynia in the rat paw," J. Neurosci. Meth. 53:55-63 (1994).
Gee et al., "The novel anticonvulsant drug, gabapentin (neurontin), binds to the $\alpha_2\delta$ subunit of a calcium channel," J. Biol. Chem. 271:5768-5776 (1996).
Kim et al., "An experimental model for peripheral neuropathy produced by segmental spinal nerve ligation in the rat," Pain 50:355-363 (1992).
Prescott, Ed., Methods in Cell Biology, vol. XIV, Academic Press, New York, N.Y. p. 33 et seq. (1976).

* cited by examiner

*Primary Examiner*—Ardin Marschel
*Assistant Examiner*—Alicia Hughes
(74) *Attorney, Agent, or Firm*—Gabryleda Ferrari-Dileo

(57) ABSTRACT

The present invention relates to a method for treating pain, reflex sympathetic dystrophy, spasticity, and bipolar disorder using ligands of the $\alpha_2\delta$ voltage-gated calcium channel, wherein the ligand comprises (2s)-aminophenyl acetic acid and derivatives.

4 Claims, No Drawings

(2S)-AMINO(PHENYL)ACETIC ACID AND DERIVATIVES AS $\alpha_2\delta$ VOLTAGE-GATED CALCIUM CHANNEL LIGANDS

TECHNICAL FIELD

The present invention is directed to the use of compounds of formula (I) as $\alpha_2\delta$ voltage-gated calcium channel ligands and to pharmaceutical compositions containing compounds of formula (I).

BACKGROUND OF THE INVENTION

Gabapentin was originally identified and developed as a treatment for seizure disorders. During its clinical and post-clinical evaluation it was discovered that this agent showed significant clinical efficacy in alleviating neuopathic pain. Gabapentin has also been combined with morphine in acute and chronic pain models.

Additionally, Gabapentin reduces tactile allodynia and hyperalgesia, both mechanical and thermal, in animal models and has shown efficacy in the treatment of reflex sympathetic dystrophy (RSD), spasticity, and bipolar disorder.

[$^3$H]Gabapentin labels human recombinant $\alpha_2\delta$ voltage-gated calcium channel with similar high affinity as compared to rat brain. [$^3$H](L)-leucine has also been shown to specifically label the $\alpha_2\delta$ subunit. Other anti-convulsant drugs like phenytoin, diazepam, carbamazepine, valproate, and phenobarbitone do not compete for gabapentin binding. Ligands for other calcium channel subtypes including verapamil, the omega-conotoxins MVIIC and GVIA, ryanodine, caffeine, capsaisin and MK801 do not interact with the gabapentin binding site. Electrophysiological data indicate that gabapentin effectively blocks Ca$^{2+}$ currents in a cortical neuron preparation and selectively reduces whole-cell Ca$^{2+}$ currents in a voltage-dependent fashion in cultured DRG neurons.

Compounds of the present invention are $\alpha_2\delta$ voltage-gated calcium channel ligands and have utility in treating or preventing disorders associated with $\alpha_2\delta$ voltage-gated calcium channels.

SUMMARY OF THE INVENTION

The present invention relates to a method of treating disorders associated with $\alpha_2\delta$ voltage-gated calcium channels in a mammal, comprising administering to the mammal a therapeutically effective amount of a compound of formula (I)

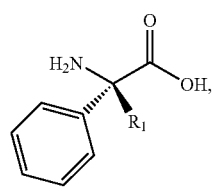

(I)

or a pharmaceutically acceptable salt, amide, ester, or prodrug thereof, wherein R$_1$ is hydrogen or alkyl.

DETAILED DESCRIPTION OF THE INVENTION

In its principle embodiment, the present invention relates to a method for treating pain in a mammal including, but not limited to, neuropathic pain, comprising administering to the mammal a therapeutically effective amount of a compound of formula (I)

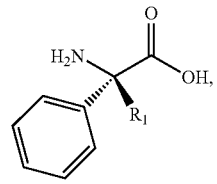

(I)

or a pharmaceutically acceptable salt, amide, ester, or prodrug thereof, wherein R$_1$ is hydrogen or alkyl.

In another embodiment, the present invention relates to a method of treating reflex sympathetic dystrophy, spasticity, or bipolar disorder, comprising administering to the mammal a therapeutically effective amount of a compound of formula (I).

In another embodiment, the present invention relates to a method of treating pain including, but not limited to, tactile allodynia, hyperalgesia, nociceptive pain, and neuropathic pain, comprising administering to the mammal a therapeutically effective amount of a compound of Formula (I).

In another embodiment, the present invention relates to a method of treating reflex sympathetic dystrophy, spasticity, or bipolar disorder, comprising administering to the mammal a therapeutically effective amount of (2S)-amino(phenyl)acetic acid.

In another embodiment, the present invention relates to a method of treating pain including, but not limited to, tactile allodynia, hyperalgesia, nociceptive pain, and neuropathic pain, comprising administering to the mammal a therapeutically effective amount of (2S)-amino(phenyl)acetic acid.

In another embodiment, the present invention relates to a method of treating pain, comprising administering to a mammal a therapeutically effective amount of a compound of formula (I) in combination with an opoid.

In another embodiment, the present invention relates to a method of treating pain, comprising administering to a mammal a therapeutically effective amount of (2S)-amino (phenyl)acetic acid in combination with an opoid.

In another embodiment, the present invention relates to a method of treating pain, comprising administering to a mammal a therapeutically effective amount of a compound of formula (I) in combination with morphine.

In another embodiment, the present invention relates to a method of treating pain, comprising administering to a mammal a therapeutically effective amount of (2S)-amino (phenyl)acetic acid in combination with morphine.

The term "alkyl" as used herein, means a straight or branched chain hydrocarbon containing from 1 to 10 carbon atoms. Preferred alkyl groups are from 1 to 4 carbon atoms. Most preferred alkyl groups are from 1-3 carbon atoms. Representative examples of alkyl include methyl, ethyl, n-propyl, and iso-propyl.

The term "nitrogen protecting group" as used herein, means those groups intended to protect an amino group against undesirable reactions during synthetic procedures. Representative nitrogen protecting groups include, but are not limited to, acetyl, benzoyl, benzyl, benzyloxycarbonyl (Cbz), formyl, phenylsulfonyl, tert-butoxycarbonyl (Boc), tert-butylacetyl, trifluoroacetyl, and triphenylmethyl (trityl).

Compounds of the present invention were named by ACD/ChemSketch version 5.0 (developed by Advanced Chemistry Development, Inc., Toronto, ON, Canada) or were given names which appeared to be consistent with ACD nomenclature.

A preferred compound of the present invention is (2S)-amino(phenyl)acetic acid.

Preparation of Compounds of the Present Invention

2-Alkylated analogues of (2S)-amino(phenyl)acetic acid can be prepared by a variety of synthetic routes. A representative procedure is shown in Schemes 1. Further, all citations herein are incorporated by reference.

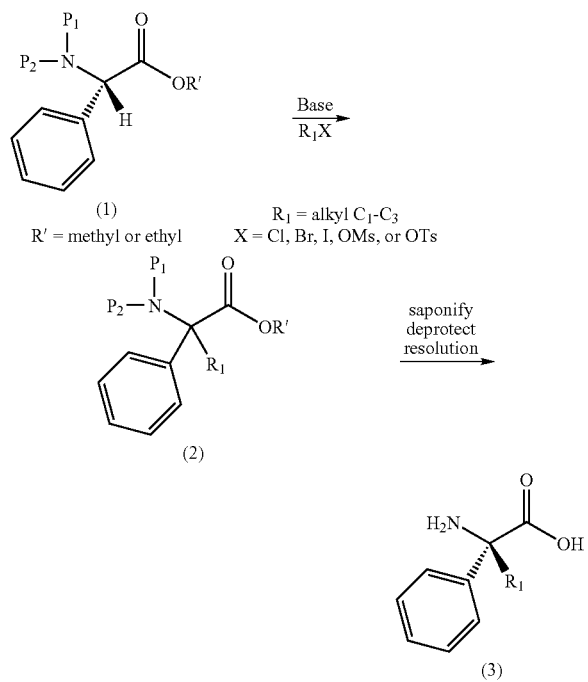

Scheme 1

Compounds of general formula (3), wherein $R_1$ is a most preferred alkyl $C_1$-$C_3$ and $P_1$ and $P_2$ are independently nitrogen protecting groups, can be prepared as described in Scheme 1. Compounds of general formula (1), purchased or prepared using methodology well known to those in the art, can be treated with a base including, but not limited to, lithium diisopropylamine, followed by treatment with an alkyl halide, alkyl mesylate, or an alkyl tosylate in a solvent including, but not limited to, diethyl ether or tetrahydrofuran to provide alkylated compounds of general formula (2). Alkylated compounds of general formula (2) can be saponified, deprotected, and resolved using methods well known to those of skill in the art. For example, resolution can be accomplished by attachment of the nitrogen or carboxy group to a chiral auxiliary, separation of the diastereomers by recrystallization or chromatography, and liberation of the optically pure product from the auxiliary. Alternatively, the enantiomers can be separated via chromatography on a chiral column. Another method of resolution involves the formation of a diastereomeric salt followed by selective recrystallization of one of the diastereomeric salts. It is to be understood that the order of saponification, deprotection or removal of the nitrogen protecting groups, and resolution of the enantiomers can be rearranged.

In Vitro Data

Binding Assay for $\alpha_2\delta$ Subunits

Mouse brains were obtained from Pel-Freez Biologicals (Rogers, Ariz.). Radioligand [4,5-$^3$H](L)-Leucine was purchased from Amersham Biosciences (Piscataway, N.J.). Polypropylene test tubes (12×75 mm, 5 mL) were purchased from Sarstedt (Newton, N.C.). Whatman GF/B paper (fired) was purchased from Brandel (Gaitherburg, Md.). EcoLume™ scintillation cocktail was purchased from ICN Biomedicals (Irvine, Calif.). All other reagents were purchased from Sigma Chemical Co (St. Louis, Mo.).

The membrane preparation is a variation of the method described in N. S. Gee, J. P. Brown, V. U. K. Dissanayake, J. Oxford, R. Thurlow, and G. N. Woodruff, J. Biol. Chem., 271:5768-5776 (1996). Twenty-five mouse cerebral corticies were removed from frozen brains, and were homogenized in 40 mL of ice-cold 320 mM sucrose, 1 mM EDTA, 1 mM EGTA, 10 mM HEPES/KOH pH 7.4 buffer solution, using a glass-Teflon homogenizer. The homogenate was centrifuged at 1000×g at 4° C. for 10 minutes. The supernatant was collected and centrifuged at 30,000×g at 4° C. for 20 minutes. The pellet was resuspended in 1 mM EDTA, 1 mM EGTA, 10 mM HEPES/KOH pH 7.4 buffer solution to a final volume of 40 mL and stirred on ice for 30 minutes. The resuspension was centrifuged at 30,000×g at 4° C. for 20 minutes. The pellet was then resuspended in 1.25 mM EDTA, 1.25 mM EGTA, 25% glycerol (v/v), 0.4% Tween 20 (v/v), HEPES/KOH pH 7.4 to a final volume of 12.5 mL and stirred on ice for 1 hour. The suspension was centrifuged at 75,000×g at 4° C. for 90 minutes. The supernatant was collected and frozen at –80° C. in 1 mL aliquots.

The [$^3$H](L)-Leucine binding assay is a variation of the methods described in Gee et al., J. Biol. Chem., 271:5768-5776 (1996) and J. P. Brown, V. U. K. Dissanayake, A. R. Briggs, M. R. Milic, and N. S. Gee, Analytical Biochemistry, 255:236-243 (1998). [$^3$H](L)-Leucine binding assays were performed in 5 mL polypropylene test tubes at room temperature. To each tube was add 25 μL double distilled (dd) H$_2$0, 125 μL of 20 mM HEPES/KOH pH 7.4, 25 μL of compound being tested (ddH$_2$0 for a total binding/(L)-Leucine for non-specific binding), 50 μL of mouse cerebral cortex membranes (40 μg/50 μl), 25 μL [$^3$H](L)-Leucine (18.8 nM [$^3$H](L)-Lecuine, approximately 270,000 CPM per tube). The total reaction volume is 250 μL. Vortex the tubes and incubate at room temperature for 45 minutes. The total reaction volume is 250 μL. Soak the GF/B filters in 0.3% Polyethylene imine (PEI) for 10 minutes prior to harvesting membranes. The membranes were harvested and washed three times with ice cold 50 mM Tris/HCl pH 7.4. Each filter was transferred to a scintillation tube and 5 mL of scintillation cocktail was added and allowed to let sit overnight before counting. The data was analyzed using GraphPad Prizm version 3.0.

Gabapentin was determined to have an IC$_{50}$ or 0.2 μM. (2S amino(phenyl)acetic acid was determined to have an IC$_{50}$ or 0.2 μM.

In Vivo Data

Determination of Analgesic Effect

Male Sprague Dawley rats (80-100 g) were purchased from Charles River (Portage, Mich.). Prior to surgery, animals were group-housed and maintained in a temperature regulated environment (lights on between 7:00 a.m. and 8:00 p.m.). Following nerve ligation surgery, animals were group housed. Two weeks after surgery, experimentation began. Rats had access to food and water ad libitum. All studies were approved by the Abbott Laboratories Institutional Animal Care and Use Committee.

Under halothane anesthesia, the L5 and L6 spinal nerves were tightly ligated in the manner described previously by S. H. Kim and J. M. Chung, PAIN 50:355 (1992). Briefly, an incision was made on the dorsal portion of the hip and the muscle was blunt dissected to reveal the spinal processes. The L6 transverse process was removed, and the left L5 and L6 spinal nerves were tightly ligated with a 5.0 braided silk suture. The wound was cleaned, the membrane sewn with a 4.0 dissolvable Vicryl suture and the skin closed with wound clips.

For the assessment of neuropathic pain, mechanical allodynia in the affected paw of animals that had undergone spinal nerve ligation was evaluated using von Frey filaments. As described previously by S. R. Chaplan, F. W. Bach, J. W. Pogrel, J. M. Chung, and T. L. Yaksh, "Quantitative assessment of tactile allodynia in the rat paw" J. Neurosci. Meth., 53:55-63(1994) two weeks following surgery, rats were acclimated to the testing box that was constructed of plexiglass with a wire mesh floor to allow access to the planter surface of the hindpaws. Using the Dixons Up-Down method, a baseline level of allodynia was determined to have a withdrawal threshold of 3 g of pressure.

Rats were placed in groups labeled A-D with six rats per group. Group A was administered 1.0 mL/kg of vehicle (100% PEG400). Group B was administered 50 μmol/kg of test compound. Group C was administered 100 μmol/kg of test compound. Group D was administered 200 μmol/kg of test compound. All vehicle and test compound doses (in vehicle) were administered orally, 60 minutes before von Frey testing. Data are expressed as the percentage of maximal protective effect relative to the control (vehicle treated) animals. The $EC_{50}$ for gabapentin was determined to be 160 μmol/kg. The $EC_{50}$ for (2S)-amino(phenyl)acetic acid was determined to be 50 μmol/kg.

The in vitro and in vivo data demonstrate that (2S)-amino (phenyl)acetic acid interacts with the $\alpha_2\delta$ voltage-gated calcium channel and that (2S)-amino(phenyl)acetic acid has an analgesic effect in an animal model of neuropathic pain.

Compounds of the present invention can be used to treat pain, tactile allodynia, hyperalgesia, reflex sympathetic dystrophy, spasticity, or bipolar disorder as described by Justin S. Bryans and David J. Wustrow, Med. Res. Rev., 19:149-177 (1999).

Compounds of the present invention can be used in combination with morphine for the treatment of acute and chronic pain as described in Justin S. Bryans and David J. Wustrow, Med. Res. Rev., 19:149-177 (1999).

The present invention also provides pharmaceutical compositions that comprise compounds of the present invention. The pharmaceutical compositions comprise compounds of the present invention formulated together with one or more nontoxic pharmaceutically acceptable carriers. The pharmaceutical compositions can be specially formulated for oral administration in solid or liquid form, for parenteral injection or for rectal administration.

The pharmaceutical compositions of this invention can be administered to humans and other mammals orally, rectally, parenterally, intracisternally, intravaginally, intraperitoneally, topically (as by powders, ointments or drops), bucally or as an oral or nasal spray. The term "parenterally," as used herein, refers to modes of administration which include intravenous, intramuscular, intraperitoneal, intrasternal, subcutaneous and intraarticular injection and infusion.

The term "pharmaceutically acceptable carrier," as used herein, means a non-toxic, inert solid, semi-solid or liquid filler, diluent, encapsulating material or formulation auxiliary of any type. Some examples of materials which can serve as pharmaceutically acceptable carriers are sugars such as, but not limited to, lactose, glucose and sucrose; starches such as, but not limited to, corn starch and potato starch; cellulose and its derivatives such as, but not limited to, sodium carboxymethyl cellulose, ethyl cellulose and cellulose acetate; powdered tragacanth; malt; gelatin; talc; excipients such as, but not limited to, cocoa butter and suppository waxes; oils such as, but not limited to, peanut oil, cottonseed oil, safflower oil, sesame oil, olive oil, corn oil and soybean oil; glycols; such a propylene glycol; esters such as, but not limited to, ethyl oleate and ethyl laurate; agar; buffering agents such as, but not limited to, magnesium hydroxide and aluminum hydroxide; alginic acid; pyrogen-free water; isotonic saline; Ringer's solution; ethyl alcohol, and phosphate buffer solutions, as well as other non-toxic compatible lubricants such as, but not limited to, sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Pharmaceutical compositions of this invention for parenteral injection comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), vegetable oils (such as olive oil), injectable organic esters (such as ethyl oleate) and suitable mixtures thereof. Proper fluidity can be maintained, for example, by the use of coating materials such as lecithin, by the maintenance of the required particle size in the case of dispersions and by the use of surfactants.

These compositions may also contain adjuvants such as preservatives, wetting agents, emulsifying agents and dispersing agents. Prevention of the action of microorganisms can be ensured by the inclusion of various antibacterial and antifungal agents, for example, paraben, chlorobutanol, phenol sorbic acid and the like. It may also be desirable to include isotonic agents such as sugars, sodium chloride and the like. Prolonged absorption of the injectable pharmaceutical form can be brought about by the inclusion of agents which delay absorption such as aluminum monostearate and gelatin.

In some cases, in order to prolong the effect of the drug, it is desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissues.

The injectable formulations can be sterilized, for example, by filtration through a bacterial-retaining filter or by incorporating sterilizing agents in the form of sterile solid compositions which can be dissolved or dispersed in sterile water or other sterile injectable medium just prior to use.

Solid dosage forms for oral administration include capsules, tablets, pills, powders and granules. In such solid dosage forms, the active compound may be mixed with at least one inert, pharmaceutically acceptable excipient or carrier, such as sodium citrate or dicalcium phosphate and/or a) fillers or extenders such as starches, lactose, sucrose, glucose, mannitol and silicic acid; b) binders such as carboxymethylcellulose, alginates, gelatin, polyvinylpyrrolidone, sucrose and acacia; c) humectants such as glycerol; d) disintegrating agents such as agar-agar, calcium carbonate, potato or tapioca starch, alginic acid, certain silicates and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay and i) lubricants such as talc, calcium stearate, magnesium stearate, solid polyethylene glycols, sodium lauryl sulfate and mixtures thereof. In the case of capsules, tablets and pills, the dosage form may also comprise buffering agents.

Solid compositions of a similar type may also be employed as fillers in soft and hard-filled gelatin capsules using such carriers as lactose or milk sugar as well as high molecular weight polyethylene glycols and the like.

The solid dosage forms of tablets, dragees, capsules, pills and granules can be prepared with coatings and shells such as enteric coatings and other coatings well known in the pharmaceutical formulating art. They may optionally contain opacifying agents and may also be of a composition such that they release the active ingredient(s) only, or preferentially, in a certain part of the intestinal tract, optionally, in a delayed manner. Examples of embedding compositions which can be used include polymeric substances and waxes.

The active compounds can also be in micro-encapsulated form, if appropriate, with one or more of the above-mentioned carriers.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor and sesame oils), glycerol, tetrahydrofurfuryl alcohol, polyethylene glycols and fatty acid esters of sorbitan and mixtures thereof.

Besides inert diluents, the oral compositions may also include adjuvants such as wetting agents, emulsifying and suspending agents, sweetening, flavoring and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar, tragacanth and mixtures thereof.

Compositions for rectal or vaginal administration are preferably suppositories which can be prepared by mixing the compounds of this invention with suitable non-irritating carriers or carriers such as cocoa butter, polyethylene glycol or a suppository wax which are solid at room temperature but liquid at body temperature and therefore melt in the rectum or vaginal cavity and release the active compound.

Compounds of the present invention can also be administered in the form of liposomes. As is known in the art, liposomes are generally derived from phospholipids or other lipid substances. Liposomes are formed by mono-or multi-lamellar hydrated liquid crystals which are dispersed in an aqueous medium. Any nontoxic, physiologically acceptable and metabolizable lipid capable of forming liposomes can be used. The present compositions in liposome form can contain, in addition to a compound of the present invention, stabilizers, preservatives, excipients and the like. The preferred lipids are natural and synthetic phospholipids and phosphatidyl cholines (lecithins) used separately or together.

Methods to form liposomes are known in the art. See, for example, Prescott, Ed., Methods in Cell Biology, Volume XIV, Academic Press, New York, N.Y. (1976), p. 33 etseq.

Dosage forms for topical administration of a compound of this invention include powders, sprays, ointments and inhalants. The active compound may be mixed under sterile conditions with a pharmaceutically acceptable carrier and any needed preservatives, buffers or propellants which may be required. Opthalmic formulations, eye ointments, powders and solutions are also contemplated as being within the scope of this invention.

Actual dosage levels of active ingredients in the pharmaceutical compositions of this invention can be varied so as to obtain an amount of the active compound(s) which is effective to achieve the desired therapeutic response for a particular patient, compositions and mode of administration. The selected dosage level will depend upon the activity of the particular compound, the route of administration, the severity of the condition being treated and the condition and prior medical history of the patient being treated.

When used in the above or other treatments, a therapeutically effective amount of one of the compounds of the present invention can be employed in pure form or, where such forms exist, in pharmaceutically acceptable salt, ester or prodrug form. The phrase "therapeutically effective amount" of the compound of the invention means a sufficient amount of the compound to treat disorders, at a reasonable benefit/risk ratio applicable to any medical treatment. It will be understood, however, that the total daily usage of the compounds and compositions of the present invention will be decided by the attending physician within the scope of sound medical judgement. The specific therapeutically effective dose level for any particular patient will depend upon a variety of factors including the disorder being treated and the severity of the disorder; activity of the specific compound employed; the specific composition employed;

the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

The compounds of the present invention can be used in the form of pharmaceutically acceptable salts derived from inorganic or organic acids. The phrase "pharmaceutically acceptable salt" means those salts which are, within the scope of sound medical judgement, suitable for use in contact with the tissues of humans and lower animals without undue toxicity, irritation, allergic response and the like and are commensurate with a reasonable benefit/risk ratio.

Pharmaceutically acceptable salts are well-known in the art. For example, S. M. Berge et al. describe pharmaceutically acceptable salts in detail in (J. Pharmaceutical Sciences, 1977, 66: 1 et seq). The salts can be prepared in situ during the final isolation and purification of the compounds of the invention or separately by reacting a free base function with a suitable organic acid. Representative acid addition salts include, but are not limited to acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, fumarate, hydrochloride, hydrobromide, hydroiodide, 2-hydroxyethansulfonate (isothionate), lactate, maleate, methanesulfonate, nicotinate, 2-naphthalenesulfonate, oxalate, palmitoate, pectinate, persulfate, 3-phenylpropionate, picrate, pivalate, propionate, succinate, tartrate, thiocyanate, phosphate, glutamate, bicarbonate, p-toluenesulfonate and undecanoate. Also, the basic nitrogen-containing groups can be quaternized with such agents as lower alkyl halides such as, but not limited to, methyl, ethyl, propyl, and butyl chlorides, bromides and iodides; dialkyl sulfates like dimethyl, diethyl, dibutyl and diamyl sulfates; long chain halides such as, but not limited to, decyl, lauryl, myristyl and stearyl chlorides, bromides and iodides; arylalkyl halides like benzyl and phenethyl bromides and others. Water or oil-soluble or dispersible products are thereby obtained. Examples of acids which can be employed to form pharmaceutically acceptable acid addition salts include such inorganic acids as hydrochloric acid, hydrobromic acid, sulfuric acid, and phosphoric acid and such organic acids as acetic acid, fumaric acid, maleic acid, 4-methylbenzenesulfonic acid, succinic acid and citric acid.

Basic addition salts can be prepared in situ during the final isolation and purification of compounds of this invention by reacting a carboxylic acid-containing moiety with a suitable base such as, but not limited to, the hydroxide, carbonate or bicarbonate of a pharmaceutically acceptable metal cation or with ammonia or an organic primary, secondary or tertiary amine. Pharmaceutically acceptable salts include, but are not limited to, cations based on alkali metals or alkaline earth metals such as, but not limited to, lithium, sodium, potassium, calcium, magnesium and aluminum salts and the like and nontoxic quaternary ammonia and amine cations including ammonium, tetramethylammonium, tetraethylammonium, methylamine, dimethylamine, trimethylamine, triethylamine, diethylamine, ethylamine and the like. Other representative organic amines useful for the formation of base addition salts include ethylenediamine, ethanolamine, diethanolamine, piperidine, piperazine and the like.

The term "pharmaceutically acceptable ester" or "ester," as used herein, refers to esters of compounds of the present invention which hydrolyze in vivo and include those that break down readily in the human body to leave the parent compound or a salt thereof. Examples of pharmaceutically acceptable, non-toxic esters of the present invention include $C_1$-to-$C_6$ alkyl esters and $C_5$-to-$C_7$ cycloalkyl esters, although $C_1$-to-$C_4$ alkyl esters are preferred. Esters of the compounds of formula I can be prepared according to conventional methods. Representative examples include, but are not limited to, methyl (2S)-amino(phenyl)acetate, ethyl (2S)-amino(phenyl)acetate, isopropyl (2S)-amino(phenyl)acetate, and tert-butyl (2S)-amino(phenyl)acetate.

The term "pharmaceutically acceptable amide" or "amide," as used herein, refers to non-toxic amides of the present invention derived from ammonia, primary $C_1$-to-$C_6$ alkyl amines and secondary $C_1$-to-$C_6$ dialkyl amines. In the case of secondary amines, the amine may also be in the form of a 5-or 6-membered heterocycle containing one nitrogen atom including, but not limited to, morpholinyl, piperidinyl, and piperazinyl. Amides derived from ammonia, $C_1$-to-$C_3$ alkyl primary amides and $C_1$-to-$C_2$ dialkyl secondary amides are preferred. Amides of the compounds of formula (I) can be prepared according to conventional methods. It is intended that amides of the present invention include amino acid and peptide derivatives of the compounds of formula (I), as well. Representative examples include, but are not limited to, (2S)-2-amino-2-phenylacetamide, (2S)-2-amino-N-methyl-2-phenylacetamide, (2S)-2-amino-N-ethyl-2-phenylacetamide, and (2S)-2-amino-N,N-dimethyl-2-phenylacetamide.

The term "pharmaceutically acceptable prodrug" or "prodrug," as used herein, represents those prodrugs of the compounds of the present invention which are, within the scope of sound medical judgement, suitable for use in contact with the tissues of humans and lower animals without undue toxicity, irritation, allergic response, and the like, commensurate with a reasonable benefit/risk ratio, and effective for their intended use. Examples of prodrugs can be glycol-like compounds and phosphate prodrugs. Prodrugs of the present invention may be rapidly transformed in vivo to compounds of formula (I), for example, by hydrolysis in blood.

The present invention contemplates compounds of formula (I) formed by synthetic means or formed by in vivo biotransformation.

The compounds of the invention can exist in unsolvated as well as solvated forms, including hydrated forms, such as hemi-hydrates. In general, the solvated forms, with pharmaceutically acceptable solvents such as water and ethanol among others are equivalent to the unsolvated forms for the purposes of the invention.

The total daily dose of the compounds of this invention administered to a human or lower animal may range from about 0.01 to about 100 mg/kg/day. For purposes of oral administration, more preferable doses can be in the range of from about 0.1 to about 125 mg/kg/day. If desired, the effective daily dose can be divided into multiple doses for purposes of administration; consequently, single dose compositions may contain such amounts or submultiples thereof to make up the daily dose.

What is claimed is:

1. A method of treating neuropathic pain, in a mammal using a ligand of the $\alpha_2\delta$ voltage-gated calcium channel, wherein the ligand is a compound of formula (I)

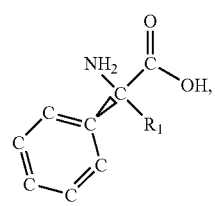

(I)

or a pharmaceutically acceptable salt, amide, or ester, thereof, wherein $R_1$ is hydrogen or alkyl.

2. A method of claim 1, comprising administering to the mammal a compound of formula (I) in combination with an opioid.

3. A method of claim 2, wherein the opioid is morphine.

4. A method according to claims 1 or 2 wherein the compound of formula (I) is (2S)-amino(phenyl)acetic acid or pharmaceutically acceptable salt thereof.

* * * * *

UNITED STATES PATENT AND TRADEMARK OFFICE
CERTIFICATE OF CORRECTION

PATENT NO.        : 7,354,955 B2
APPLICATION NO.  : 10/752943
DATED            : April 8, 2008
INVENTOR(S)      : Lee et al.

Page 1 of 1

It is certified that error appears in the above-identified patent and that said Letters Patent is hereby corrected as shown below:

Column 1, line 66, "In its principle embodiment" to read as --In its principal embodiment--

Column 2, line 41, "with an opoid" to read as --with an opioid--

Column 2, line 45, "with an opoid" to read as --with an opioid--

Column 8, line 39, "Opthalmic formulations" to read as --Ophthalmic formulations--

Signed and Sealed this

Twenty-third Day of November, 2010

David J. Kappos
*Director of the United States Patent and Trademark Office*